(12) United States Patent
Chang et al.

(10) Patent No.: US 6,649,089 B2
(45) Date of Patent: Nov. 18, 2003

(54) RED ORGANIC ELECTROLUMINESCENT MATERIALS

(75) Inventors: Min-Jong Chang, Hsinchu (TW); Wen-Yao Huang, Ming-Jian Hsiang (TW); Wen-Chin Huang, Taipei (TW)

(73) Assignee: E-Ray Optoelectronics Technology Co., Ltd., Taipei (TW)

( * ) Notice: Subject to any disclaimer, the term of this patent is extended or adjusted under 35 U.S.C. 154(b) by 0 days.

(21) Appl. No.: 10/348,405

(22) Filed: Jan. 20, 2003

(65) Prior Publication Data

US 2003/0193043 A1 Oct. 16, 2003

(30) Foreign Application Priority Data

Feb. 22, 2002 (TW) .......................... 91103079 A (51) Int. Cl.[7] ...................... C09K 11/06; C07D 405/02; C07D 455/04
(52) U.S. Cl. ...................... 252/301.16; 546/94; 546/95; 428/690; 428/917; 252/301.22; 252/301.26; 252/301.32
(58) Field of Search ...................... 252/301.16, 301.22, 252/301.26, 301.32; 428/690, 917; 546/94, 95

(56) References Cited

U.S. PATENT DOCUMENTS

5,908,581 A * 6/1999 Chen et al. ............ 252/301.16

* cited by examiner

Primary Examiner—Charanjit S. Aulakh
(74) Attorney, Agent, or Firm—Dellett and Walters (57) ABSTRACT

A red fluorescent material comprising a compound of Formula I:

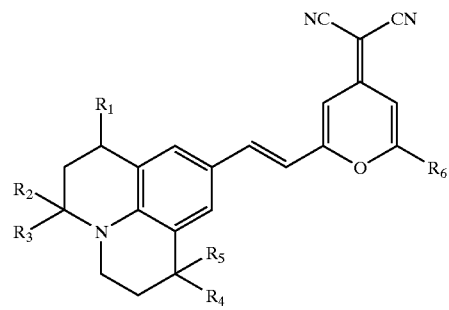

(Formula I)

wherein $R_1$, $R_2$, $R_3$, $R_4$, $R_5$, and $R_6$ each independently represents a linear or branched aliphatic group having from 1 to 10 carbon atoms or an aromatic group having from 5 to 20 carbon atoms.

7 Claims, 4 Drawing Sheets

Fig. 1

| 4a: R=methyl | (DCJP) |
| 4b: R=ethyl | (DCJPE) |
| 4c: R=i-propyl | (DCJPI) |
| 4d: R=t-butyl | (DCJPB) |
| 4e: R=mesityl | (DCJPM) |
| 4f: R=1-naphthyl | (DCJPN) |

RED ORGANIC ELECTROLUMINESCENT MATERIALS

FIELD OF THE INVENTION

This invention relates to red fluorescent materials that can be used as dopants in organic electroluminescent devices.

BACKGROUND OF THE INVENTION

One of the applications for using red fluorescent materials is in organic EL (electroluminescent) devices. Organic EL devices are known to be highly efficient and are capable of producing a wide range of colors. Useful applications such as flat-panel displays have been contemplated and commercialization is well underway. Representative of earlier organic EL devices are Gurnee et al., U.S. Pat. No. 3,172,862, issued Mar. 9, 1965; Gurnee, U.S. Pat. No. 3,173,050, issued Mar. 9, 1965; Dresner, "Double Injection Electroluminescence in Anthracene," RCA Review, Vol. 30, pp. 322–334, 1969; and Dresner,. U.S. Pat. No. 3,710,167, issued Jan. 9, 1973. Typical organic emitting materials were formed of a conjugated organic host material and a conjugated organic activating agent having condensed benzene rings. The organic emitting material was present as a single layer medium having a thickness much above 1 micrometer. Thus, this organic EL medium was highly resistive and the EL device required a relatively high voltage (>100 volts) to operate.

The most recent discoveries in the art of organic EL device construction have resulted in devices having the organic EL medium consisting of extremely thin layers (<1.0 micrometer in combined thickness) separating the anode and cathode. Herein, the organic EL medium is defined as the organic composition between the anode and cathode electrodes. Typically, organic EL devices are composed of three layers of organic molecules that are interposed between a transparent electrode and a metallic electrode. The three layers include an electron-transporting layer, a luminescent layer and a hole-transporting layer. The luminescent layer between the electron-transporting and hole-transporting layers provides an efficient site for the recombination of the injected hole-electron pair and resultant electroluminescence. A hole-injecting layer may be added to reduce the driving voltage. Optionally a hole- or electron-blocking layer may be added to improve the luminance efficiency. An organic EL device comprising four to six layers of organic molecules is thus obtained.

The extremely thin organic EL medium offers reduced resistance, permitting higher current densities for a given level of electrical bias voltage. Since light emission is directly related to current density through the organic EL medium, the thin layers coupled with increased charge injection and transport efficiencies have allowed acceptable light emission levels to be achieved with low applied voltages in ranges compatible with integrated circuit drivers, such as field effect transistors.

Organic EL devices have lower driving voltages and have been shown applicable for use in full-color flat-panel displays. The investigation in organic EL devices and materials has attracted a lot of worldwide attention and investment. The improvements in organic EL devices such as color, stability, efficiency and fabrication methods have been disclosed in U.S. Pat. Nos.: 5,151,629; 5,150,006; 5,141,671; 5,073,446; 5,061,569; 5,059,862; 5,059,861; 5,047,687; 5,104,740; 5,227,252; 5,256,945; 5,069,975; 5,122,711; 5,366,811; 5,126,214; 5,142,343; 5,389,444; 5,458,977; 5,908,581; 5,935,720; 6,091,195.

One of the ultimate objectives of the developments in organic light-emitting diodes (OLED) is the application in full color flat-panel displays. Therefore, obtaining three primary colors of red, green and blue that meet commercial requirements is critical in the product applications of OLED. In current developments, one of the most commonly used methods to modify the color and luminance efficiency is by doping a small amount of a highly fluorescent material into the main EL emitter as a dopant. In this manner, lights of three primary colors of red, green and blue can be obtained. Accordingly, seeking perfect doping materials of red, green and blue (RGB) and improving the luminous efficiency, luminance and chromaticity of the RGB colors have become one of the most important research objectives. Among the three primary colors of lights, the research for a primary red light is most problematic.

The organic EL mechanism utilizes the energy transfer between the host and guest materials. For example, a red organic EL emission can be obtained by doping a small amount of a red fluorescent material (a guest) into tris-(8-hydroxyquinolinato)aluminum ($Alq_3$) (the host) to transfer the green luminescent energy of $Alq_3$ to the red guest (see U.S. Pat. No. 4,769,292). In the current red fluorescent dopants, a series of materials developed by Eastman Kodak Company of the U.S. are most notable (see U.S. Pat. No. 5,908,581). $Alq_3$ is a suitable host for red EL emitters since its emission at 530 nm is adequate to sensitize guest EL emission in the red spectral region.

The photoluminescent efficiency of the earliest red guest dye, 4-(dicyano-methylene)-2-methyl-6-(p-dimethylaminostyryl)4-pyran (DCM), (Formula A) is 78% at $\lambda_{max}$=596 nm in a reasonable doping concentration (about 0.5%). The light emitted is a yellow-biased red. Subsequently, Kodak developed a julolidyl derivative DCJ red guest material (Formula B) which emits light with a peak wavelength within the red-range of 610~690 nm. The $Alq_3$-based EL emitter has a maximum luminous intensity when doped with 0.57% of DCJ. However, the color of the light emitted is reddish orange due to the green luminescence of $Alq_3$ that was not totally quenched. While more saturated red luminescence can be obtained when DCJ doped into the emitter is >4% of the emitter, the luminance efficiency drops to 50% of that with the maximum luminous intensity. This is because the red guest dyes aggregate and influence each other at high concentrations, which leads to the quenching of the luminescence.

DCM (A)

(B)

DCJ

Other considerations in the fields of fluorescence and electroluminescence applications are the purity of fluorescent materials and the degree of synthetic complexities, including consideration of yield loss due to post-process purification procedures. In the aforementioned patents, the preparation and subsequent purification of both DCM and DCJ are complicated by the inevitable generation of a significant amount of an unwanted corresponding bis-condensed dye caused by the further reaction of the "active" methyl group present in the fluorescent dye molecules (see Hammond, *Optics Comm.*, 1989, 29, 331). Furthermore, once the bis-condensed dye is formed in the reaction mixture, it is difficult to be removed and tends to diminish or extinguish DCM (or DCJ) fluorescence.

To reduce the quenching of the guest dye per se and correspondingly raise the luminance efficiency, Kodak developed derivatives which are based on tetra-methyljulolidine (DCJT) (Formula C) (see Chen et al., *Proc. 2$^{nd}$ Internat. Sym. Chem. Functional Dyes*. 1992, 536). They have four more methyl groups than DCJ. Thereby, the methyl groups result in a steric hindrance between dye molecules, and thus reduce the quenching effect caused by the formation of aggregate due to high concentration.

While DCJT has a good luminance efficiency, the controlling of synthesis and purification remains a problem. The reactive methyl group at the C-6 position of pyran moiety of the DCJT product may further react with the starting material tetramethyljulolidyl aldehyde to produce the by-product, bis-DCJT (Formula D). (See C. H. Chen, C. W. Tang, J. Shi and K. P. Klubek, *Macromol. Symp.* 125, 49 1997.) Therefore, the preparation and subsequent purification of DCJT are also complicated by the inevitable generation of significant amount of the unwanted bis-condensed dye that tends to decrease the fluorescence efficiency of DCJT.

(C)

DCJT

(D)

bis-DCJT

To overcome this problem, C. H. Chen et al. (see U.S. Pat. No. 5,908,581, issued Jun. 1, 1999, entitled "Red Organic Electroluminescent Materials" and U.S. Pat. No. 5,935,720, issued Aug. 10, 1999, entitled "Red Organic Electroluminescent Devices") synthesized what appeared to be the first asymmetric 4-(dicyanomethylene)-2-methyl-4H-pyran, from which derivatives of DCJTR can be prepared without the reactive methyl group on the C-6 position of pyran moiety (Formula E). The DCJTR derivatives include DCJTP (R=phenyl), DCJTE (R=ethyl), DCJTB (R=t-butyl), DCJTM (R=mesityl) and the like. The syntheses of those derivatives produce no (or less) bis-condensed by-products contaminant, and the purity can be above 98%.

(E)

DCJTR

Since 4-(dicyanomethylene)-2-tert-butyl-6-(1,1,7,7-tetramethyljulolidyl-9-enyl)-4H-pyran (DCJTB) has good luminance, the red luminescent devices produced by doping (1%–4% by volume) of the compound into the main EL emitters will meet the preliminary requirement of commercial applications. Currently, companies such as Kodak and Sanyo have applied the compounds to red organic EL devices.

However, the red EL devices produced by doping the main EL emitter with DCJTB have some drawbacks. The main disadvantage is that the required doping concentration of DCJTB is up to 2–4% if the hue of light emission is to be tuned to the CIE red position in standard displays. High concentrations of dopants will give rise to the quenching of fluorescence, resulting in low luminance. In particular, among most of the current OLED RGB primary colors, the luminance efficiency of red light is poor.

In addition, the yield of the key intermediate tetramethyljulolidine in the synthesis of DCJTR is low. The reaction yield depends on the types and reaction conditions of acidic catalysts (see C. H. Chen, S.-W. Wen, P. Balaganesan, *Third International Conference on Electroluminescence of Molecular Materials and related phenomena*, Sept. 5–8, 2001, L.A., Calif., U.S.A., Abstract: O-51).

Therefore, in the red organic electroluminescent devices, there exits the need to improve the EL performance of the fluorescent dopant material; to improve the overall yield of the red dopant material, in particular, the key intermediate, tetramethyljulolidine synthesis; and to improve the purification process of the red dopant by sublimation.

SUMMARY OF THE INVENTION

This invention replaces the four methyl groups of DCJTR with five strategically positioned aliphatic or aromatic groups with the intention to alleviate the fluorescence-quenching problem of the dye at high concentration. It is expected that the interaction between molecules of the dye will be lessened due to the enhanced steric interaction that may reduce the propensity for dye aggregation at high concentration.

The red fluorescent dopants, 4-(dicyanomethylene)-2-$R_6$-(1,3,3,7,7-penta-methyljulolidyl-9-enyl)-4H-pyran (DCJPR, Formula I) series of compounds, according to the present invention are prepared by a new reaction route that is different from and better than that of DCJTR. In particular, the yield of the intermediate pentamethyljulolidine of DCJPR of the present invention is significantly higher than that of the intermediate tetramethyljulolidine of DCJTR. As a result, the overall reaction yield of DCJPR is far better than that of DCJTR thereby offers the advantage of producing the red dopant more cost effective.

When compared under similar doping concentrations, it was found that the new dopant DCJPB (Formula I, R=t-Bu) offers higher luminance yield than that of DCJTB at the similar chromaticity. In addition, DCJPB having a lower melting point than that of DCJTB is easier to purify by train sublimation without incurring thermal-induced decomposition.

It is another objective of the present invention to provide an improved red fluorescent material which fluoresces in the red region of the visible spectrum.

It is another objective of the present invention to provide an improved red fluorescent material which offers higher reaction yield and easier purification and mass production capabilities.

This objective is achieved by a red fluorescent material comprising a compound of formula I:

Formula I wherein $R_1$, $R_2$, $R_3$, $R_4$, $R_5$, and $R_6$ each independently represents a linear or branched aliphatic group having from 1 to 10 carbon atoms or an aromatic group having from 5 to 20 carbon atoms.

This objective is also achieved by a red fluorescent material comprising a compound of formula II:

Formula II wherein $R_1$, $R_2$, and $R_3$ each independently represents a linear or branched aliphatic group having from 1 to 10 carbon atoms or an aromatic group having from 5 to 20 carbon atoms.

This objective is also achieved by a red fluorescent material comprising a compound of Formula III:

Formula III wherein R represents a linear or branched aliphatic group having from 1 to 10 carbon atoms or an aromatic group having from 5 to 20 carbon atoms.

The red fluorescent dopants, 4-(dicyanomethylene)-2-$R_6$-(1,3,3,7,7-penta-methyljulolidyl-9-enyl)-4H-pyran (DCJPR), are prepared by a new reaction route different from that of DCJTR. The yield of the intermediate pentarnethyl-julolidine of DCJPR of the present invention is significantly higher than that of the intermediate tetramethyljulolidine of DCJTR. Therefore, the purification and quantitative production of DCJPR are easier than that of DCJTR.

It is a feature of the present invention that when the compound is applied to EL devices it provides a fluorescent compound devoid of chemical reactivity of the extra "active" methyl group, thereby avoiding the formation of the unwanted bis-condensed dye in the reaction product mixture. Moreover, in the properties of organic EL devices under the same doping concentrations, DCJPB has a thermal stability similar to DCJTB, but a better luminous efficiency and an almost same chromaticity.

When used as a dye material in other devices such as dye lasers and luminescent solar concentrators, fluorescent inks and other applications, the material is particularly useful.

BRIEF DESCRIPTION OF THE DRAWINGS

These and other advantages of this invention can be better appreciated by reference to the following detailed description considered in conjunction with the drawings in which.

DETAILED DESCRIPTION OF THE PREFERRED EMBODIMENTS

Figure 1:
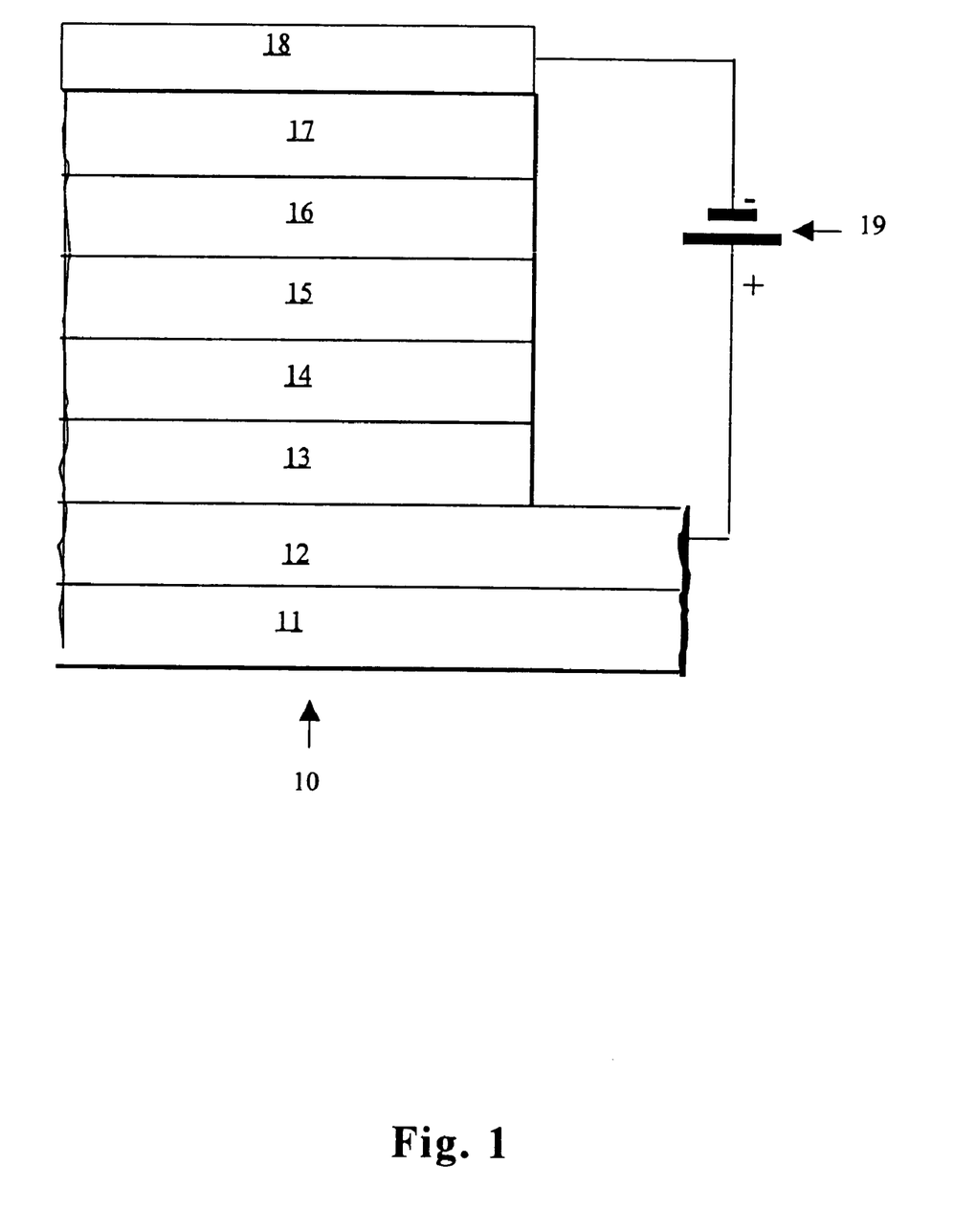
FIG. 1 is a schematic diagram of the multilayer structures of the organic EL device according to the invention.

One particularly useful application of the compound is in EL devices. An EL device 10, which uses a compound according to the invention, is schematically illustrated in FIG. 1. The organic electroluminescent device (OLED) 10 comprises a transparent substrate 11, an anode layer 12, a hole-injecting layer 13, a hole-transporting layer 14, a luminescent layer 15, an electron-transporting layer 16, an electron-injecting layer 17 and a cathode layer 18. The transparent substrate 11 is glass or plastic. The anode layer 12 is transparent and electroconductive and is deposited on the surface of the substrate 11. A hole-injecting material is deposited on the surface of the anode layer 12 to form the hole-injecting layer 13. Subsequently, a hole-transporting material is deposited on the surface of the hole-injecting layer 13 to form a hole-transporting layer 14. The organic luminescent layer 15 made of luminescent material containing fluorescent dopants (a guest) is deposited on the surface of the layer 14. The electron-transporting layer 16 made of electron-transporting materials is deposited on the surface of the organic luminescent layer 15. Next, the electron-injecting layer 17 made of electron-injecting materials is deposited on the surface of the electron-transporting layer 16, and the cathode layer 18 made of metal is deposited on the surface of the electron-injecting layer 17 to form a cathode. The anode layer 12 is a p-type contact whereas the cathode layer 18 is an n-type contact.

A power supply (19) with a negative end (−) and a positive end (+) provides an electric potential to the OLED device (10). The cathode layer 18 of the OLED device (10) is connected to the negative end (−) of power supply 19, and the anode layer 12 is connected to the positive end (+). When a potential is applied between the anode layer 12 and the cathode layer 18 by the power supply 19, the electron ejected from the n-type contact (cathode layer 18) will pass into the organic luminescent layer 15 through the electron-injecting layer 17 and organic electron-transporting layer 16. The hole ejected from the p-type contact (anode layer 12) will pass into the organic luminescent layer 15 through the organic hole-injecting layer 13 and organic hole-transporting layer 14. When the electron and hole recombined in the organic luminescent layer 15, energy is released in part as light, thus producing electroluminescence.

The region where the hole and electron recombine is known as the recombination zone. The five-layer device structure is designed specifically to confine the recombination at the vicinity near the interface between the hole-transport and the electron-transport layer where the probability for producing electroluminescence is the highest. The recombination confinement scheme for two-layer device structure has been disclosed by Tang and Van Slyke (*Applied Physics Letters*, Vol. 51, 913, 1987) and is done by choosing carrier injecting electrodes of suitable work-functions and transport materials of a proper carrier mobility. Away from this interface between the organic layers and in particular at or near the injecting electrodes, the recombination of hole and electron would generally be much less radiate due to the effect of radiate quenching by a conducting surface.

One objective of the invention is to provide highly efficient fluorescent dopants for used in organic electroluminescent devices. The fluorescent dopant for the luminescent layer (15) comprises a compound represented by Formula I, Formula I wherein $R_1$, $R_2$, $R_3$, $R_4$, $R_5$, and $R_6$ each independently represents a linear or branched aliphatic group having from 1 to 10 carbon atoms or an aromatic group having from 5 to 20 carbon atoms.

In compounds of Formula I, $R_1$, $R_2$, $R_3$, $R_4$, and $R_5$ can each independently be methyl, ethyl, propyl, n-butyl, i-propyl; aryl or heteroaryl, or including, phenyl and, furyl, thienyl, pyridyl, and other heterocyclic systems; or halogen substititents such as chloro and fluoro, and $R_6$ can be ethyl, propyl, n-butyl, i-propyl, t-butyl, sec-butyl, t-amyl, neopentyl and the like; sterically hindered aryl, for example, 1-naphthyl, 9-anthracenyl, pyrenyl, perylenyl, ortho-substituted aryl of 1–10 carbon atoms, including mesityl, 2,4-dimethylphenyl, 2-methylphenyl and the like; or perhaloalkyl of 1–10 carbon atoms, including trifluoromethyl, pentafluoroethyl, perfluoroalkyl and the like.

One objective of the invention is to provide highly efficient fluorescent dopants for used in organic electroluminescent devices. The fluorescent dopant for the luminescent layer (15) comprises a compound represented by Formula I

Formula II wherein $R_1$, $R_2$, and $R_3$ each independently represents a linear or branched aliphatic group having from 1 to 10 carbon atoms or an aromatic group having from 5 to 20 carbon atoms.

In compounds of Formula II, $R_1$ and $R_2$ can each independently be methyl, ethyl, propyl, n-butyl, i-propyl; aryl or heteroaryl, or including, phenyl and, furyl, thienyl, pyridyl, and other heterocyclic systems; or halogen substituents such as chloro and fluoro, and $R_3$ can be ethyl, propyl, n-butyl, i-propyl, t-butyl, sec-butyl, t-amyl, neopentyl and the like; sterically hindered aryl, for example, 1-naphthyl, 9-anthracenyl, pyrenyl, perylenyl, ortho-substituted aryl of 1–10 carbon atoms, including mesityl, 2,4-dimethylphenyl, 2-methylphenyl and the like; or perhaloalkyl of from carbon atoms, including trifluoromethyl, pentafluoroethyl, perfluoroalkyl and the like.

One objective of the invention is to provide highly efficient fluorescent dopants for used in organic electroluminescent devices. The fluorescent dopant for the luminescent layer (15) comprises a compound represented by Formula III,

Formula III wherein R represents a linear or branched aliphatic group having from 1 to 10 carbon atoms or an aromatic group having from 5 to 20 carbon atoms.

In compounds of Formula III, R can be ethyl, propyl, n-butyl, i-propyl, t-butyl, sec-butyl, t-amyl, neopentyl and the like; sterically hindered aryl, for example, 1-naphthyl, 9-anthracenyl, pyrenyl, perylenyl, ortho-substituted aryl of 1–10 carbon atoms, including mesityl, 2,4-dimethylphenyl, 2-methylphenyl and the like; or perhaloalkyl of 1–10 carbon atoms, including trifluoromethyl, pentafluoroethyl, perfluoroalkyl and the like.

The substrate for the EL devices 10 is electrically insulating and light transparent. The light transparent property is desirable for viewing the EL emission through the substrate. For applications where the EL emission is viewed through the top electrode, the transmission characteristic of the support is immaterial, and therefore any appropriate substrate such as opaque semiconductor and ceramic wafers can be used. Of course, it is necessary to provide in these device configurations a light transparent top electrode.

In the embodiments, the electron-transporting layer or host emitter of OLED 10 is composed of one of the following materials:

Alq₃

BeBq₂

B-Alq

ZnSPB

ZnOPB

Almq₃

TAZ-1

TAZ-2

TPBI

Hole-transporting layer (14) is composed of an aromatic tertiary amine, which is a compound containing at least one trivalent nitrogen atom that is bonded only to carbon atoms, at least one of which is a member of an aromatic ring (see U.S. Pat. Nos. 3,180,730; 3,567,450; 3,658,520). Examples of the compounds are given as follows.

NPB

TPD

HTM-2

CBP

-continued

DPS p-mmDPS p-dmDPS

-continued

Aromatic amine I

Aromatic amine II

Aromatic amine III

Spiro-TPD

Hole-injecting layer (13) is composed of one of the following materials:

m-MTDATA

CuPc

α-TNATA

β-TNATA

PEDT/PSS $[CF_x]_n$

The luminescent layer of the organic EL medium comprises of a luminescent or fluorescent material where electroluminescence is produced as a result of electron-hole pair recombination in this region. In the simplest construction, the luminescent layer comprises of a single component, that is a pure material with a high fluorescent efficiency. A well known material is tris(8-quinolinato)-aluminum, (Alq$_3$), which produces excellent green electroluminescence. A preferred embodiment of the luminescent layer comprises a multi-component material consisting of a host material doped with one or more components of fluorescent dyes. Using this method, highly efficient EL devices can be constructed. Simultaneously, the color of the EL devices can be tuned by using fluorescent dyes of different emission wavelengths in a common host material. This dopant scheme has been described in considerable details for EL devices using Alq$_3$ as the host material by Tang et al. [see U.S. Pat. No. 4,769,292].

An important relationship for choosing a fluorescent dye as a dopant capable of modifying the hue of light emission when present in a host material is a comparison of their bandgap potential which is defined as the energy difference between the highest occupied molecular orbital and the lowest unoccupied molecular orbital of the molecule. For efficient energy transfer from the host to the dopant molecules, a necessary condition is that the bandgap of the dopant is smaller than that of the host material. An advantage of using a green host such as Alq$_3$ is that its bandgap is sufficiently large to effect energy transfer to fluorescent dyes emitting in the red, such as DCJTR and improves red fluorescent compounds described in this invention. In the practice of the present invention, the host material forming the EL luminescent layer where light is emitted in response to electron-hole recombination comprises of $Alq_3$.

The preferred materials for the multi-layered organic EL device are each capable of film-forming, i.e., capable of being fabricated as a continuous layer having a thickness of less than 5000 Å. A preferred method for forming the organic EL element is by vacuum vapor deposition. Extremely thin defect-free continuous layers can be formed by this method. The overall thickness of the organic EL element must be at least 1000 Å.

Another method for forming thin films in EL devices in accordance with the present invention include spin-coating, ink jet printing, or screen printing from a solution containing the EL material.

In the EL device in accordance with the present invention, the material used to form the substrate is preferably transparent and can be selected from glass, transparent plastic or quartz. Use of a metal such as gold, aluminum, indium, magnesium, copper, silver and the like, alloys or mixtures of these metals is preferred for the anode. Use of transparent materials such as indium tin oxide (ITO), $SnO_2$, $ZnO$ and the like is preferred for the cathode. ITO is a mixture of indium oxide and tin oxide.

The anode and cathode of the organic EL device can each take any convenient conventional form. Where the intention is to transmit light from the organic EL device through the anode, this can be conveniently achieved by coating a thin conductive layer onto a transparent substrate, e.g., a transparent or substantially transparent glass plate or plastic film.

Conductive polymers and glass or plastics coated with a conductive polymer can also be used as the substrate.

Polymers can be deposited on the cathode by conventional methods e.g. by vacuum evaporation, spin coating, chemical deposition, direct electrodeposition, etc. Preferably the thickness of the polymer layer is such that the layer is conductive and transparent and is from 20 nm to 200 nm.

The EL material can be deposited on the substrate directly by vacuum evaporation or evaporation of an organic solvent from a solution containing EL material. The solvent which is used will depend on the material and chlorinated hydrocarbons such as dichloromethane and N-methylpyrrolidone; dimethyl sulphoxide; tetrahydrofuran; dimethylformamide etc. are suitable in many cases.

Alternatively, electroluminescent material can be deposited by spin coating from a solution, or by vacuum deposition from the solid state e.g. sputtering or any other conventional methods can be used.

The following is a partial list with the chemical structure of examples of red doping materials that meet the requirements for the invention.

DCJP

DCJPE

DCJPI

DCJPB

DCJPM

DCJPN

To reduce the quenching of DCJTB at high concentration, the present invention replaces the four methyl groups of DCJTB with five strategically positioned aliphatic groups or aromatic groups to hinder interactions between the molecules in the dye. Several embodiments of the organic electroluminescent devices are produced by doping a compound such as one of the compounds exemplified above into the Alq$_3$ host emitter.

The red organic electroluminescent devices were fabricated by doping DCJTB and DCJPB respectively into the Alq$_3$ host emitter, as shown in FIG. 1. The effect of various doping concentrations on the chromaticity (CIE coordinates x and y) and luminance efficiency (cd/A) of the devices were measured.

Figure 2:
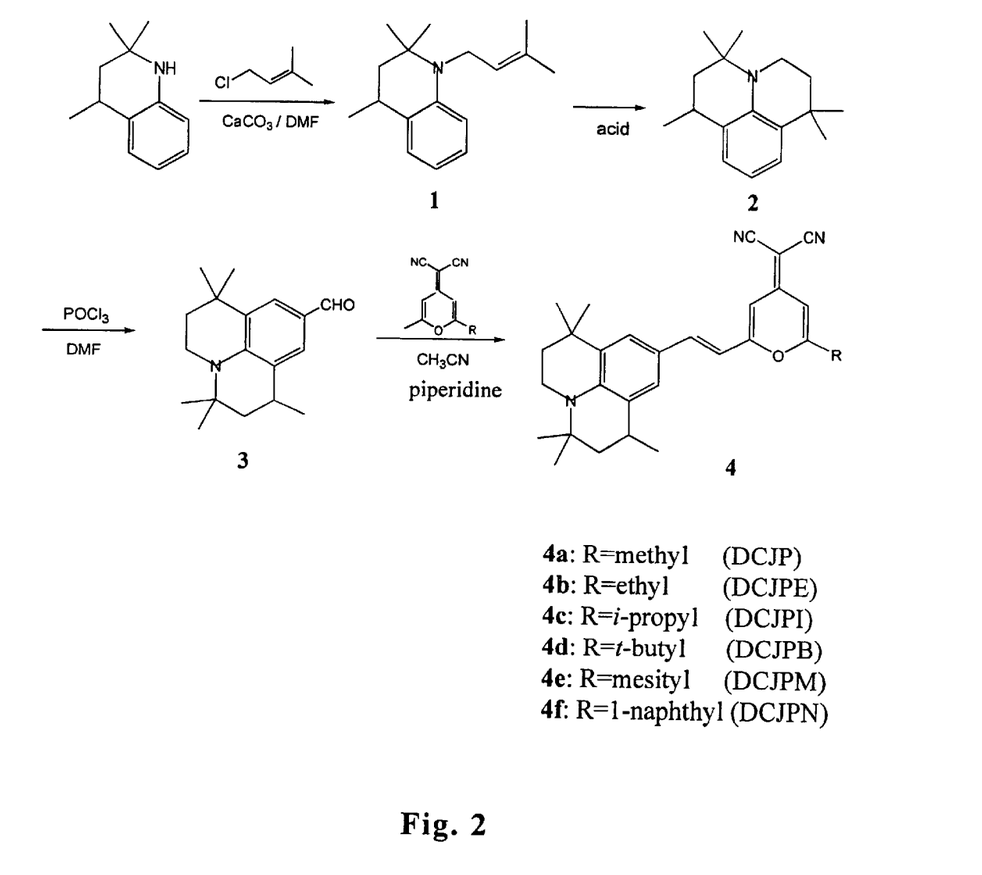
FIG. 2 is a scheme for the synthesis of the red fluorescent dopants, DCJPR, of the invention.

The features of the organic electroluminescent devices fabricated by the red fluorescent dopants, DCJPR series of materials, are described more specifically as follows:

1. The development of new reaction routes and synthesis processes:

The present invention replaces the tetramethyljulolidyl aldehyde of DCJTR series material with the pentamethyljulolidyl aldehyde of DCJPR. The starting materials and the entire route of the reaction sequence (FIG. 2) are better and improved from those used in the syntheses of DCJTR.

2. The yield of DCJPR is significantly higher than that of DJCTR:

The yield of the key intermediate tetramethyljulolidine was low in the synthesis of DCJTR which depended greatly on the types of catalysts and reaction conditions (see, C. H. Chen, S.-W. Wen, P. Balaganesan, *Third International Conference on Flectroluminescence of Molecular Materials and Related Phenomena*, Sept. 5–8, 2001, L.A., Calif., U.S.A., Abstract: O-15). The key step affecting the low yield was the bis-cyclization for the double ring closure to form tetramethyljulolidine of DCJTR and was only about 30%. On the contrary, the yield of the cyclization for forming the intermediate pentamethyljulolidine of DCJPR can be as high as 91% (as in the synthesis of compound 2 described in the Examples). With such a yield, the purification and quantitative production of DCJPR were therefore much more efficient and cost effective than those of DCJTR.

3. The thermal properties of DCJPB are comparable to DCJTB

The thermal properties of the red fluorescent dopants in accordance with the present invention, DCJPR, were compared with those of DCJTB. The results are listed in Table I.

TABLE I

The Comparison of Thermal Properties between DCJPR and DCJTB

| Compounds | Thermal Decomposition Temperature $T_d$ (° C.) | Glass Transition Temperature $T_g$ (° C.) | Melting Temperature $T_m$ (° C.) |
| --- | --- | --- | --- |
| DCJTB | 368 | 110 | 299 |
| DCJP | 321 | 107 | 250 |
| DCJPE | 333 | 85 | 277 |
| DCJPI | 351 | 89 | 270 |
| DCJPB | 356 | 106 | 269 |
| DCJPM | 374 | 120 | 265 |
| DCJPN | 356 | 124 | 294 |

As shown from the results in the comparison of thermal properties (Table I), the thermal decomposition temperatures of the red fluorescent dopants in accordance with the present invention, DCJPR, are all above 300° C., which are significantly higher than the useful highest temperature of general OLED devices (about 85° C.). Therefore, the thermal stability of the DCJPR series materials meets the requirements for OLED devices. In addition, the melting temperatures of DCJPR series materials are about 250~294° C. depending on the specific R group. Except for 250° C. with DCJP and 294° C. with DCJPN, there are no significant differences between the melting temperatures of the remaining dopants.

4. The optical properties of DCJPB are comparable to DCJTB

DCJPB and DCJTB were dissolved in 1,2-dichloroethane to compare the optical properties of the red fluorescent dopants in accordance with the present invention, DCJPR, with DCJTB. The maximum absorption peak, maximum radiance peak and relative radiant intensity of DCJPR are compared to DCJTB. The results are listed in Table II.

TABLE II

The Optical Properties of Inventive Red Fluorescent Dopants, DCJPR, and DCJTB

| Red fluorescent dopants | Maximum absorption peak $\lambda_{abs.}$ (nm)$^a$ | Maximum radiance peak $\lambda_{max.}$ (nm)$^a$ | Relative fluorescent intensity (Radiance)$^b$ |
| --- | --- | --- | --- |
| DCJTB | 507 | 624 | 1.00 |
| DCJP | 507 | 624 | 0.87 |
| DCJPE | 508 | 625 | 0.86 |
| DCJPI | 507 | 625 | 0.93 |
| DCJPB | 507 | 624 | 0.95 |
| DCJPM | 524 | 635 | 0.82 |
| DCJPN | 526 | 668 | 0.04 |

$^a$in 1,2-dichloroethane
$^b$relative to DCJTB

The results in Table II shows that the maximum absorption peaks of the DCJPB and DCJPI with the superior fluorescent radiance occurred at 507 nm (the same as DCJTB). This absorption peak region is close to the maximum radiance peak of Alq$_3$ (about 525 nm). Therefore, as in the application of DCJTB, Alq$_3$ may be used as the electroluminescent source and the host luminescent material for DCJPB and. DCJPI whereby the maximum emission peaks for DCJPB and DCJPI both occurred at about 625 nm. As shown by the above experimental results, replacing the tetramethyljulolidyl aldehyde of DCJTB by the pentamethyljulolidyl aldehyde of DCJPB does not affect the luminescent peak and luminance efficiency of DCJTB. This is probably because the pentamethyljulolidyl group retains the conjugated planar property of the tetramethyl-julolidyl group. The relative fluorescent efficiencies of DCJPB and DCJPI calculated by taking the fluorescent efficiency of DCJTB as 1.0 are both about 0.95, which is not significantly different from DCJTB.

Similar to DCJTR series materials, the naphthyl group of DCJPN will increase the conjugation of DCJP and lead to a low luminescent energy (i.e. the luminous wavelength is longer than the wavelength of red light). DCJPM has a better luminance efficiency and is nearer the luminous wavelength of red light than DCJPN because the mesityl group is twisted away from the conjugated plane of DCJP, which restricts its free rotation. However, a luminous peak of 635 nm is still too red. In contrast, tert-butyl and iso-propyl of DCJPB and DCJPI, respectively, do not substantially affect the luminous peak of DCJP. DCJPB and DCJPI both have a luminance efficiency similar to that of DCJTB.

5. The EL performance of DCJPB is comparable to that of DCJTB

Figure 3:
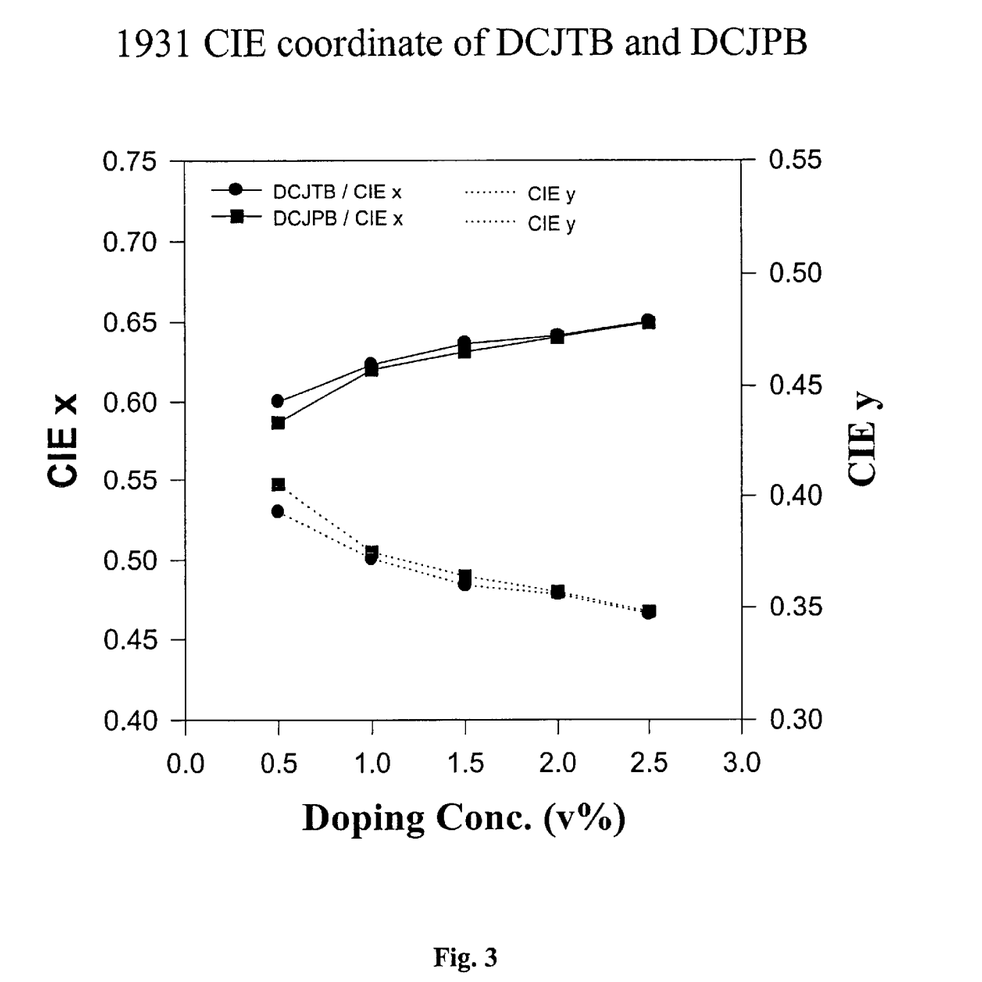
FIG. 3 shows the effect of the doping concentrations of DCJTB and DCJPB to the luminescent colors of the 1931 coordinates CIE x and CIE y, respectively.

FIG. 3 shows that the luminous chromaticity of DCJTB and DCJPB approaches and moves into the range of red (CIE coordinates x=0.63~0.65 and y=0.35~0.37) as the doping concentrations increase. The color of DCJPB was similar to that of DCJTB under the same doping concentration when both devices have at least 1.5% doping concentration, which is the minimum amount required to obtain red color.

Figure 4:
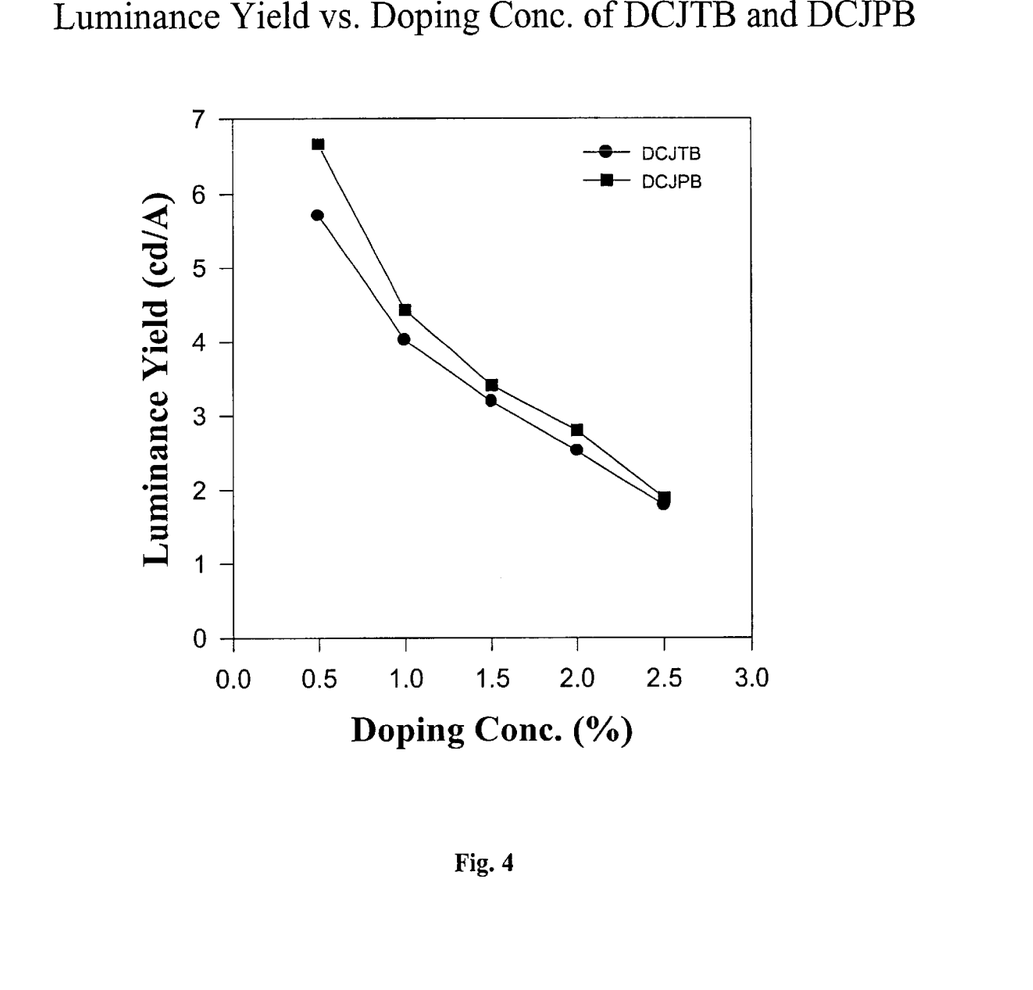
FIG. 4 shows the effect of the doping concentrations of DCJTB and DCJPB to the luminance yield.

FIG. 4 shows that the luminance efficiency of DCJTB and DCJPB decreased when the doping concentrations increased (from 0.5% to 2.5%) due to the quenching of fluorescence caused by the higher doping concentrations. Under same doping concentrations, the luminance efficiency of DCJPB was better than that of DCJTB. This indicates that a better luminance yield was achieved by replacing the four methyl groups of DCJTB (that was designed to reduce the quenching of dye) with five methyl groups to hinder the inter molecular interactions of the dye.

As shown by the above experimental results, the DCJPR series of materials in accordance with the present invention can be used as red fluorescent dopants in OLEDs. In particular, under the same doping concentrations, DCJPB has better luminance efficiencies and similar luminescent chromaticities compared to those of DCJTB, while DCJPB has a overall synthesis yield significantly higher than the state-of-the-art red dopant of DCJTB.

EXAMPLES

The invention and its advantages are further illustrated by reference to the following Examples in conjunction with the figures. The synthetic procedures in Examples 1–6 refer to FIG. 2.

Example 1

Synthesis of Compound 4a (DCJP) Synthesis of Compound 1

23.5 g of 1-chloro-3-methyl-butene and 28 g of calcium carbonate was added to a solution of 28 g of 2,2,4-trimethyl-1,2,3,4-tetrahydroquinoline (the detailed synthesis of 2,2,4-trimethyl-1,2,3,4-tetrahydroquinoline can be found in U.S. Pat. No. 3,247,211) in 200 mL of DMF. The reaction mixture was stirred at room temperature for 3 hours. The reaction mixture was then extracted with diethyl ether and water. The organic layer obtained was dried over $MgSO_4$, concentrated and purified by chromatography using ethyl acetate/hexane (1/8) as the eluent to give 36.7 g of brown liquid. Yield: 94%.

Synthesis of Compound 2

A solution of 25 g of compound 1 in 200 mL of concentrated sulfuric acid was stirred at room temperature for 4 hours. The mixture was poured onto pieces of ice, neutralized with an ammonium hydroxide aqueous solution and then extracted with diethyl ether. The organic layer obtained was dried over $MgSO_4$, concentrated and purified by chromatography using ethyl acetate/hexane (1/10) as the eluent to give 22.8 g of brown liquid. Yield: 91%.

Synthesis of Compound 3

A solution of 20 g of compound 2 in 150 mL of DMF on an ice/water bath was added dropwise 44 mL of phosphorus oxychloride under a nitrogen atmosphere. After complete addition, the mixture was stirred at room temperature for 6 hours. The mixture was poured onto pieces of ice, neutralized with an ammonium hydroxide aqueous solution and then extracted with diethyl ether. The organic layer obtained was dried over $MgSO_4$, concentrated and purified by chromatography using ethyl acetate/hexane (1/10) as the eluent to give 21.1 g of brown liquid. Yield: 95%.

Synthesis of Compound 4a

A solution containing 18 g of compound 3, 0.1 g of piperidine, 11.4 g of 2-(2,6-dimethyl-4H-4-pyranyliden) malononitrile (the synthesis procedure was reported by Chen et al, Macromol. Symp. 125, 49, 1997) and 250 mL of acetonitrile was stirred at 45° C. for 5 hours. The mixture was diluted with water and then extracted with diethyl ether. The organic layer obtained was dried over $MgSO_4$, concentrated and purified by chromatography using ethyl acetate/hexane (1/8) as the eluent to give 23.1 g of red solid. Yield: 82%. Mp: 250° C.

Example 2

Synthesis of Compound 4b (DCJPE)

A solution containing 20 g of compound 3, 0.1 g of piperidine, 13.7 g of 2-(2-ethyl-6-methyl-4H-4-pyranyliden) malononitrile and 250 mL of acetonitrile was stirred at 45° C. for 4 hours. The mixture was diluted with water and then extracted with diethyl ether. The organic layer obtained was dried over $MgSO_4$, concentrated and purified by passing through a silica gel column using ethyl acetate/hexane (1/7) as the eluent to give 25.9 g of red solid. Yield: 80%. Mp: 276° C.

Example 3

Synthesis of Compound 4c (DCJPI)

A solution containing 18.5 g of compound 3, 0.1 g of piperidine, 13.6 g of 2-(2-isopropyl-6-methyl-4H-4-pyranyliden) malononitrile (the synthesis procedure was reported by Chen et al., Thin Solid Films 363, 327, 2000) and 250 mL of acetonitrile was stirred at 45° C. for 5 hours. The mixture was diluted with water and then extracted with diethyl ether. The organic layer obtained was dried over $MgSO_4$, concentrated and purified by passing through a silica gel column using ethyl acetate/hexane (1/7) as the eluent to give 25.9 g of red solid. Yield: 84%. Mp: 269° C.

Example 4

Synthesis of Compound 4d (DCJPB)

A solution containing 19.1 g of compound 3, 0.1 g of piperidine, 15.0 g of 2-(2-tert-butyl-6-methyl-4H-4-pyranyliden) malononitrile and 250 mL of acetonitrile was stirred at 45° C. for 6 hours. The mixture was diluted with water and then extracted with diethyl ether. The organic layer obtained was dried over $MgSO_4$, concentrated and purified by passing through a silica gel column using ethyl acetate/hexane (1/7) as the eluent to give 27.9 g of red solid. Yield: 85%. Mp: 269° C.

Example 5

Synthesis of Compound 4e (DCJPM)

A solution containing 20 g of compound 3, 0.1 g of piperidine, 2.03 g of 2-(2-mesityl-6-methyl-4H4-pyranyliden) malononitrile and 250 mL of acetonitrile was stirred at 45° C. for 5 hours. The mixture was diluted with water and then extracted with diethyl ether. The organic layer obtained was dried over $MgSO_4$, concentrated and purified by passing through a silica gel column using ethyl acetate/hexane (1/7) as the eluent to give 30.4 g of red solid. Yield: 78%. Mp: 264° C.

Example 6

Synthesis of Compound 4f (DCJPN)

A solution containing 20 g of compound 3, 0.1 g of piperidine, 21 g of 2-(2-methyl-6-naphthyl-4H-4-pyranyliden) malononitrile and 250 mL of acetonitrile was stirred at 45° C. for 6 hours. The mixture was diluted with water and then extracted with diethyl ether. The organic layer obtained was dried over $MgSO_4$, concentrated and purified by passing through a silica gel column using ethyl acetate/hexane (1/7) as the eluent to give 31.7 g of red solid. Yield: 80%. Mp: 293° C.

Comparative Example 1

Synthesis of DCJTB

A solution containing 2 g of 1,1,7,7-tetramethyljulolidine-9-aldehyde (the synthesis procedure can be referred to in (1)

U.S. Pat. No. 5,935,720; (2) C. H. Chen, S.-W. Wen, P. Balaganesan, *Third International Conference on Electroluminescence of Molecular Materials and related phenomena*, Sept. 5–8, 2001, L.S., Calif., U.S.A., Abstract: O-51), 0.1 g of piperidine, 0.38 g of 2-(2-tert-buthyl-6-methyl-4H-4-pyranyliden) malononitrile and 5 mL of acetonitrile was stirred at reflux for 24 hours. The mixture was diluted with water and then extracted with diethyl ether. The organic layer obtained was dried over $MgSO_4$ and concentrated. The crude product was purified by recrystallization to give 0.7 g of red solid. Mp: 298° C.

Example 7

Fabrication and Measurement of the DCJP Device (Structure A)

Refer to FIG. 1 for the schematic diagram of the multilayer structures of the organic EL device according to the invention. Examples 7–10 for the organic EL devices of the invention were constructed in the following manner, respectively.

(a) An indium tin oxide (ITO) coated glass substrate was sequentially treated by a commercial detergent, rinsed in deionized water, degreased in an organic solvent and dried. After the surface was treated with a plasma processor, the ITO glass substrate was placed under a high vacuum to subject the thin film to evaporation deposition.

(b) A hole-injecting layer of CuPc having a thickness of 150 Å was deposited onto the surface of the ITO coated glass by evaporation from a tantalum boat.

(c) A hole-transporting layer of NPB having a thickness of 600 Å was deposited onto the CuPc layer, also by evaporation from a tantalum boat.

(d) The host emitter $Alq_3$ and the dopant DCJP were co-deposited onto the NPB layer by evaporation from a tantalum boat. A luminescent layer having a thickness of 375 Å was thus formed, wherein the DCJP was 1% by volume of $Alq_3$.

(e) An electron-transporting layer of $Alq_3$ having a thickness of 375 Å was deposited onto the luminescent layer by evaporation from a tantalum boat.

(f) An electron-injecting layer of LiF having a thickness of 10 Å was deposited onto the electron-transporting layer of $Alq_3$ by evaporation from a tantalum boat.

(g) A cathode layer of Aluminum with a thickness of 2000 Å was deposited by evaporation on top of the LiF layer.

(h) A DC current was passed through the device fabricated as described above, and the current-voltage-luminance and their EL efficiency were measured by photocolorimeter.

The performance of the DCJP EL device when it was driven by a current source at 20 $mA/cm^2$ is tabulated as follows:

| | |
|---|---|
| Driving voltage (volts) | 10.31 |
| Luminance (cd/m$^2$) | 333.0 |
| Luminance efficiency (cd/A) | 1.66 |
| Luminous intensity (W/Sr/m$^2$) | 1.47 |
| 1931 CIE coordinate x | 0.622 |
| 1931 CIE coordinate y | 0.375 |
| Peak wavelength (nm) | 620 |
| Width of peak (nm) | 88 |

Example 8

Fabrication and Measurement of the DCJPE Device

The DCJPE device was fabricated using the steps described in Example 7, except that DCJPE was used instead of DCJP.

The performance of the DCJPE EL device when it was driven by a current source at 20 $mA/cm^2$ is tabulated as follows:

| | |
|---|---|
| Driving voltage (volts) | 9.64 |
| Luminance (cd/m$^2$) | 319.0 |
| Luminance efficiency (cd/A) | 1.59 |
| Luminous intensity (W/Sr/m$^2$) | 1.42 |
| 1931 CIE coordinate x | 0.619 |
| 1931 CIE coordinate y | 0.376 |
| Peak wavelength (nm) | 620 |
| Width of peak (nm) | 88 |

Example 9

Fabrication and Measurement of DCJPI Device

The DCJPI device was fabricated using the steps described in Example 7, except that DCJPI was used instead of DCJP.

The performance of the DCJPI EL device when it was driven by a current source at 20 $mA/cm^2$ is tabulated as follows:

| | |
|---|---|
| Driving voltage (volts) | 9.86 |
| Luminance (cd/m$^2$) | 253.4 |
| Luminance efficiency (cd/A) | 1.27 |
| Luminous intensity (W/Sr/m$^2$) | 1.16 |
| 1931 CIE coordinate x | 0.622 |
| 1931 CIE coordinate y | 0.375 |
| Peak wavelength (nm) | 620 |
| Width of peak (nm) | 92 |

Example 10

Fabrication and Measurement of DCJPM Element

The DCJPM device was fabricated using the steps described in Example 7, except that DCJPM was used instead of DCJP.

The performance of the DCJPM EL device when it was driven by a current source at 20 $mA/cm^2$ is tabulated as follows:

| | |
|---|---|
| Driving voltage (volts) | 10.45 |
| Luminance (cd/m$^2$) | 257.7 |
| Luminance efficiency (cd/A) | 1.29 |
| Luminous intensity (W/Sr/m$^2$) | 1.43 |
| 1931 CIE coordinate x | 0.628 |
| 1931 CIE coordinate y | 0.363 |
| Peak wavelength (nm) | 628 |
| Width of peak (nm) | 92 |

Example 11

Fabrication and Measurement of the DCJPB Device (Structure B)

Refer to FIG. 1 for the schematic diagram of the multilayer structures of the organic EL device according to the invention. Example 11 for the organic EL devices of the invention and a Comparative Example 2 were constructed in the following manner, respectively.

(a) An indium tin oxide (ITO) coated glass substrate was sequentially treated by a commercial detergent, rinsed in deionized water, degreased in an organic solvent and dried. After the surface was treated with a plasma processor, the ITO glass substrate was placed under a high vacuum to subject the thin film to evaporation deposition.

(b) A hole-injecting layer of $(CF)_x$ having a thickness of 500 Å was deposited onto the surface of the ITO coated glass by plasma treatment of $CHF_3$ following a procedure published by Hang et al. [*Applied Physics Letters*, Vol. 78, 673, 2001].

(c) A hole-transporting layer of NPB having a thickness of 1200 Å was deposited onto the $CHF_3$ layer, by evaporation from a tantalum boat.

(d) The host emitter $Alq_3$ and the dopant DCJPB were co-deposited onto the NPB layer by evaporation from a tantalum boat. A luminescent layer having a thickness of 300 Å was thus formed, wherein the DCJPB was 1% by volume of $Alq_3$.

(e) An electron-transporting layer of $Alq_3$ having a thickness of 550 Å was deposited onto the luminescent layer by evaporation from a tantalum boat.

(f) An electron-injecting layer of LiF having a thickness of 10 Å was deposited onto the electron-transporting layer of $Alq_3$ by evaporation from a tantalum boat.

(g) A cathode layer of Aluminum with a thickness of 2000 Å was deposited by evaporation on top of the LiF layer.

(h) A DC current was passed through the device fabricated as described above, and the current-voltage-luminance and their EL efficiency were measured by photocolorimeter.

The performance of the DCJPB (1%) EL device when it was driven by a current source at 20 mA/cm² is tabulated as follows:

| | |
|---|---|
| Driving voltage (volts) | 8.79 |
| Luminance (cd/m²) | 886.3 |
| Luminance efficiency (cd/A) | 4.43 |
| Luminous intensity (W/Sr/m²) | 3.843 |
| 1931 CIE coordinate x | 0.620 |
| 1931 CIE coordinate y | 0.375 |
| Peak wavelength (nm) | 624 |
| Width of peak (nm) | 84 |

The DCJPB devices with 0.5–2.5%-doping concentrations by volume of $Alq_3$ were fabricated using the same steps.

Comparative Example 2

Fabrication and Measurement of DCJTB Device (Structure B)

The DCJTB device was fabricated using the steps described in Example 11, except that DCJTB was used instead of DCJPB, and DCJTB is 0.5–2.5% by volume of $Alq_3$.

The performance of the DCJTB (1%) EL device when it was driven by a current source at 20 mA/cm² is tabulated as follows:

| | |
|---|---|
| Driving voltage (volts) | 9.04 |
| Luminance (cd/m²) | 803.8 |
| Luminance efficiency (cd/A) | 4.02 |
| Luminous intensity (W/Sr/m²) | 3.547 |
| 1931 CIE coordinate x | 0.623 |
| 1931 CIE coordinate y | 0.372 |
| Peak wavelength (nm) | 624 |
| Width of peak (nm) | 84 |

The DCJTB devices with 0.5–2.5%-doping concentrations by volume of $Alq_3$ were fabricated using the same steps.

Even though characteristics and advantages of the present invention have been set forth in the foregoing description, together with details of the structure and function of the invention, the disclosure is illustrative only, and changes may be made within the scope and spirit of the invention to the full extent indicated by the broad general meaning of the terms in which the appended claims are expressed.

Parts List

10 OLED device
11 Substrate
12 Anode
13 Hole-injecting layer
14 Hole-transporting layer
15 Organic EL medium
16 Electron-transporting layer
17 Electron-injecting layer
18 Cathode
19 Power supply

What is claimed is:

1. A compound of Formula I:

(Formula I)

wherein $R_1$, $R_2$, $R_3$, $R_4$, $R_5$, and $R_6$ each independently represents a linear or branched aliphatic group having from 1 to 10 carbon atoms or an aromatic group having from 5 to 20 carbon atoms.

2. A compound of Formula II:

(Formula II)

wherein $R_1$, $R_2$, and $R_3$ each independently represents a linear or branched aliphatic group having from 1 to 10 carbon atoms or an aromatic group having from 5 to 20 carbon atoms.

3. A compound of Formula III:

(Formula III)

wherein R represents a linear or branched aliphatic group having from 1 to 10 carbon atoms or an aromatic group having from 5 to 20 carbon atoms.

4. The compounds according to claim 3, which are:

DCJP

DCJPE

DCJPI

DCJPB

DCJPM

DCJPN

5. A red fluorescent material comprising a compound according to claim 1.

6. A red fluorescent material comprising a compound according to claim 2.

7. A red fluorescent material comprising a compound according to claim 3.

* * * * *